United States Patent
Hu et al.

(10) Patent No.: US 9,824,176 B2
(45) Date of Patent: Nov. 21, 2017

(54) OPTICAL CRITICAL DIMENSION TARGET DESIGN

(71) Applicant: Nanometrics Incorporated, Milpitas, CA (US)

(72) Inventors: Jiangtao Hu, Sunnyvale, CA (US); Bingqing Li, Singapore (SG); Zhuan Liu, Fremont, CA (US)

(73) Assignee: Nanometrics Incorporated, Milpitas, CA (US)

( * ) Notice: Subject to any disclaimer, the term of this patent is extended or adjusted under 35 U.S.C. 154(b) by 105 days.

(21) Appl. No.: 14/809,061

(22) Filed: Jul. 24, 2015

(65) Prior Publication Data

US 2017/0024509 A1    Jan. 26, 2017

(51) Int. Cl.
| | | |
|---|---|---|
| *G06F 17/50* | (2006.01) | |
| *G01N 21/956* | (2006.01) | |
| *G03F 7/20* | (2006.01) | |
| *H01L 21/66* | (2006.01) | |

(52) U.S. Cl.
CPC ....... *G06F 17/5081* (2013.01); *G01N 21/956* (2013.01); *G03F 7/70625* (2013.01); *G03F 7/70683* (2013.01); *G01B 2210/56* (2013.01); *H01L 22/30* (2013.01)

(58) Field of Classification Search
CPC .. G06F 17/5081; G03F 7/70625; G03F 7/705; H01L 22/30; G01N 21/9501; G01B 2210/56
USPC ......................................................... 716/52
See application file for complete search history.

(56) References Cited

U.S. PATENT DOCUMENTS

| | | |
|---|---|---|
| 8,126,694 B2 | 2/2012 | Liu et al. |
| 8,832,611 B2 | 9/2014 | Liu et al. |
| 2008/0072207 A1 | 3/2008 | Verma et al. |

(Continued)

FOREIGN PATENT DOCUMENTS

WO    WO 2017/019251 A1    2/2017

OTHER PUBLICATIONS

International Search Report and Written Opinion for PCT Application No. PCT/US2016/040403, mailed Dec. 8, 2016.

(Continued)

*Primary Examiner* — Paul Dinh
(74) *Attorney, Agent, or Firm* — Silicon Valley Patent Group LLP

(57) ABSTRACT

A measurement target for a semiconductor device is designed. The semiconductor device includes a structure to be measured that has a spectrum response that is comparable to or below system noise level for an optical critical dimension measurement device to be used to measure the structure. The measurement target is designed by obtaining a process window and design rules for the semiconductor device and determining prospective pitches through modeling to identify pitches that produce a spectrum response from the structures that is at least 10 times greater than a system noise level for the optical critical dimension measurement device. A resonance window for each prospective pitch is determined and robustness of the resonance window is determined through modeling. Pitches of the array are selected based on the prospective pitches, resonance windows, and robustness. The target design may accordingly be produced and used to generate a measurement target.

11 Claims, 13 Drawing Sheets

(56) References Cited

U.S. PATENT DOCUMENTS

2010/0175033 A1* 7/2010 Adel ................ G03F 7/705
                                                          716/52
2011/0231167 A1   9/2011 Cramer et al.
2013/0222795 A1   8/2013 Madsen et al.
2015/0185625 A1   7/2015 Chen et al.

OTHER PUBLICATIONS

Anat Marchelli et al: "Overlay mark optimization using the KTD signal simulation system", Proceedings of Spie, vol. 7272, Mar. 13, 2009.
Taiwan Office Action mailed Feb. 22, 2017, for Taiwan Application No. 105123315.

* cited by examiner

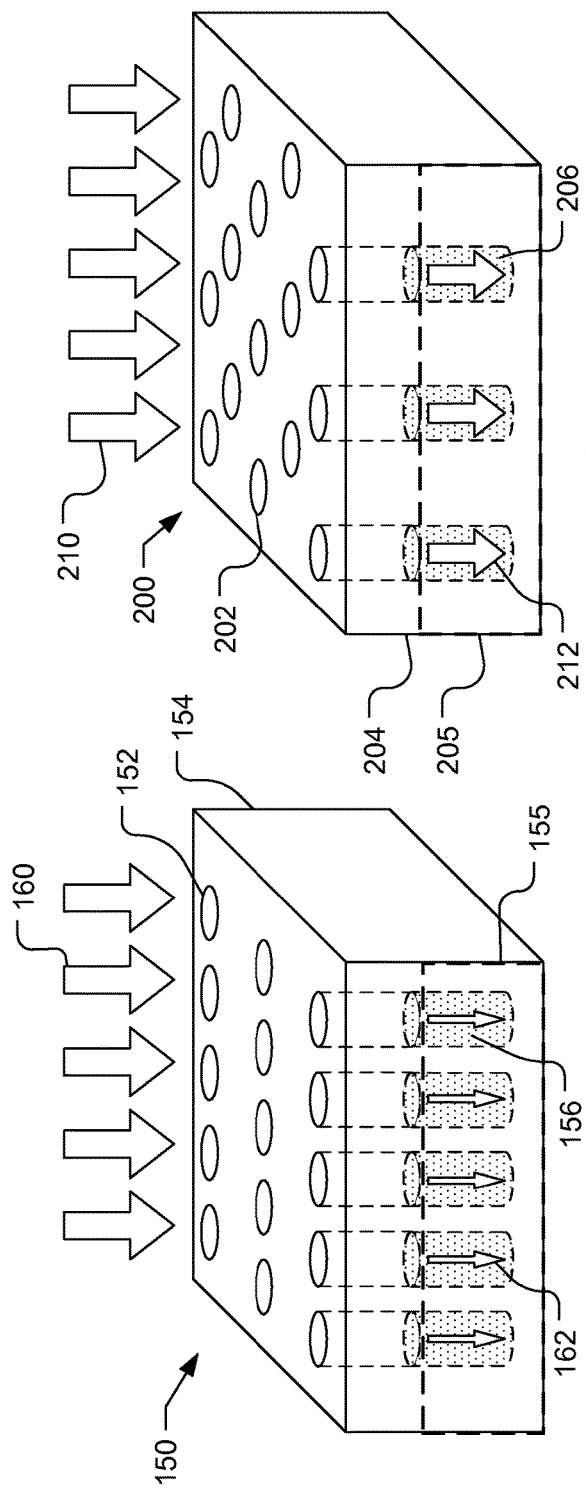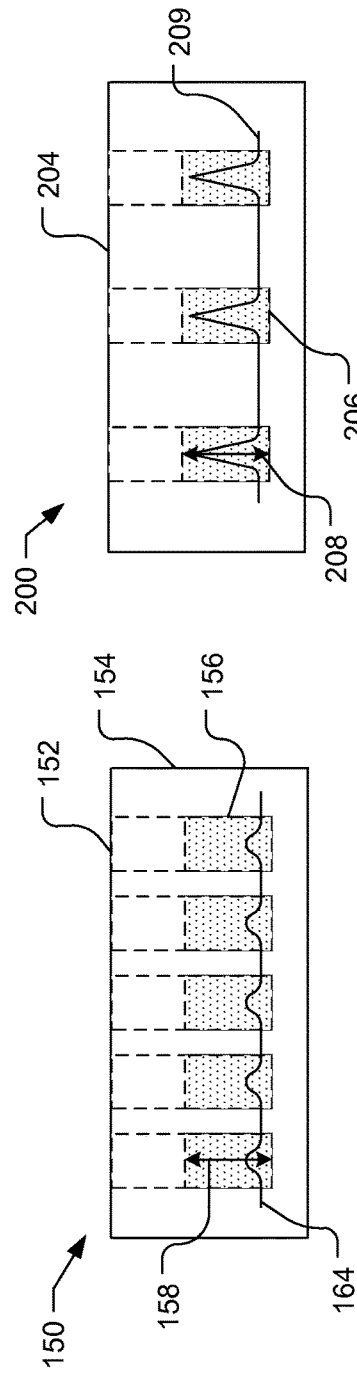

OPTICAL CRITICAL DIMENSION TARGET DESIGN

BACKGROUND

Background Field

Embodiments of the subject matter described herein are related generally to optical metrology, and more particularly to target design and manufacture for optical critical dimension metrology.

Relevant Background

During the production of semiconductor devices, such as integrated circuits, it is desirable to measure the circuit structures. Optical metrology tools are particularly well suited for measuring microelectronic structures because they are nondestructive, accurate, repeatable, fast, and inexpensive. The critical dimension of structures, such as gratings, trenches, and contact and holes is often of interest. Optical critical dimension (OCD) metrology, for example, is often used with three-dimensional semiconductor devices.

Typically, OCD metrology utilizes an OCD target that is fabricated at the same time as the structure under test and includes the same features to be characterized. The OCD target, for example, may be produced in a scribe line between semiconductor chips or in otherwise available areas of the chip. Conventional methods of OCD metrology include, e.g., reflectometry, scatterometry, and ellipsometry. These metrology methods can often accurately measure features on an upper surface of a device, but in many cases, the presence of an absorbing layer reduces or eliminates the measurement signal strength from the structures that are below the absorbing layer. Additionally, conventional methods of OCD metrology are often unsatisfactory in accurately determining the bottom CD profile of high aspect ratio structures, both in one dimensional gratings (e.g. deep narrow trenches) and in two dimensional arrays (e.g. contact and via holes). This is particularly true as the CD decreases far below the wavelength of the incident light.

SUMMARY

A measurement target for a semiconductor device is designed. The semiconductor device includes a structure to be measured that has a spectrum response that is comparable to or below system noise level for an optical critical dimension measurement device to be used to measure the structure. The measurement target is designed by obtaining a process window and design rules for the semiconductor device and determining prospective pitches through modeling to identify pitches that produce a spectrum response from the structures that is at least 10 times greater than a system noise level for the optical critical dimension measurement device. A resonance window for each prospective pitch is determined and robustness of the resonance window is determined through modeling. Pitches of the array are selected based on the prospective pitches, resonance windows, and robustness. The target design may accordingly be produced and used to generate a measurement target.

BRIEF DESCRIPTION OF THE DRAWINGS

FIG. 2A illustrates a conventional OCD target for a 3D semiconductor device.

FIG. 2B illustrates light intensity distribution for the OCD target of FIG. 2A.

FIG. 3A illustrates an OCD target similar to the OCD target of FIG. 2A, but that has been 200 altered as discussed herein.

FIG. 3B illustrates light intensity distribution for the OCD target of FIG. 3A.

DETAILED DESCRIPTION

Figure 1:
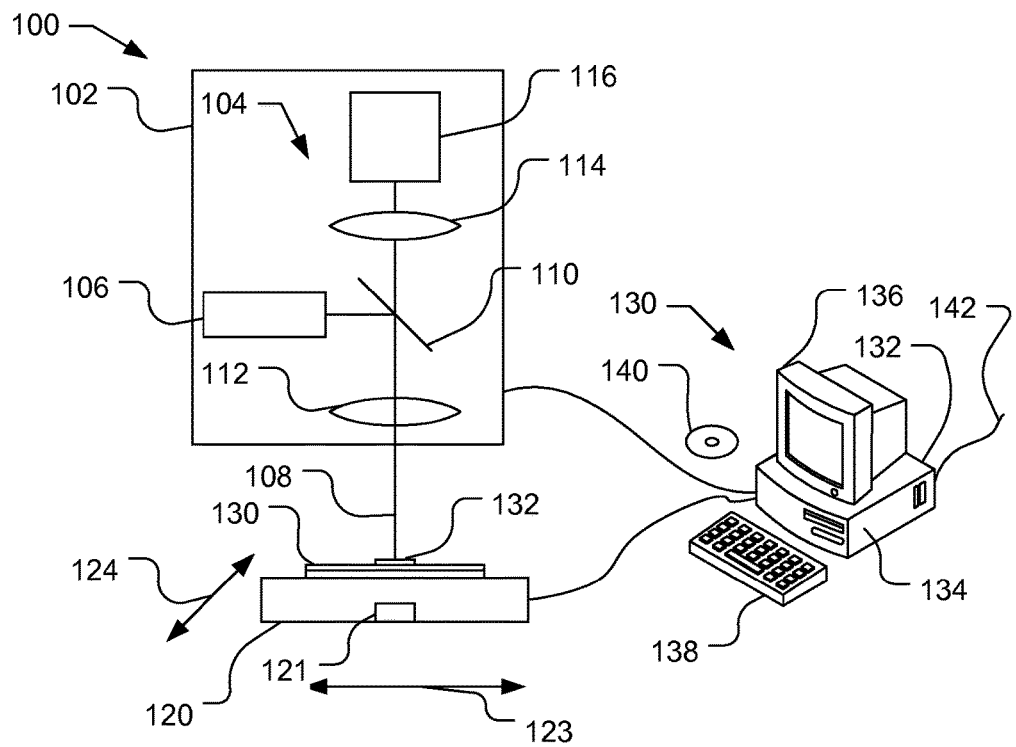
FIG. 1 shows a schematic view of an optical metrology device that performs spectroscopic optical critical dimension (OCD) metrology using a measurement target produced as described herein.

FIG. 1 shows a schematic view of an optical metrology device 100, including an optical head 102 coupled to a computer 130, such as a workstation, a personal computer, central processing unit or other adequate computer system, or multiple systems, that performs spectroscopic optical critical dimension (OCD) metrology using an OCD target 132 in accordance with one or more embodiments as described herein. The optical metrology device 100 illustrated in FIG. 1 is, e.g., a normal incidence spectroscopic reflectometer. If desired, multiple optical heads, i.e., different metrology devices, may be combined in the same metrology device 100. The computer 130 may also control the movement of a stage 120 that holds the sample 130 via actuators 121 and/or the optical head 102. The stage 120 may be capable of horizontal motion in either Cartesian (i.e., X and Y) coordinates, as indicated by arrows 123 and 124, or Polar (i.e., R and θ) coordinates or some combination of the two. The stage 120 and/or optical head 102 may also be capable of vertical motion, e.g., for focusing.

The optical head 102 may include an optical system 104 including a broadband light source 106, such as a Xenon Arc lamp and/or a Deuterium lamp, and a detector 116, such as a spectrometer. In operation, light produced by the light source 106 may be directed along an optical axis 108, e.g., via beam splitter 110, toward the sample 130 which includes the target 132. An objective 112 focuses the light onto the target 132 and receives light that is reflected from the target 132. The reflected light may pass through the beam splitter 110 and is focused with lens 114 onto the detector 116. The detector 116 provides a spectroscopic signal to the computer 130. The objective 112, beam splitter 110, lens 114, and detector 116 are merely illustrative of typical optical elements that may be used. Additional optical elements, such as a polarizer and/or analyzer, may be used if desired. Moreover, generally, additional optical elements such as field stops, lenses, etc. may be present in the optical system 104.

The computer 130 includes a processor 132 with memory 134, as well as a user interface including e.g., a display 136 and input devices 138. The spectra obtained by the optical metrology device 100 may be stored at least temporarily in memory 134 or in non-transitory computer-usable storage medium 140. Additionally, non-transitory computer-usable storage medium 140 may have computer-readable program code embodied thereon and may be used by the computer 130 for causing the processor to control the metrology device 100 and to determine the desired characteristics of the target 132 using the spectra received from the optical metrology device 100. The computer-usable storage medium 140 may be, but is not limited to, magnetic and optical storage devices such as disk drives, magnetic tape, compact discs, and DVDs (digital versatile discs or digital video discs). A communication port 142 may also be used to receive instructions that are stored in memory 134 or other storage in computer 130 and used to program the computer 130 to perform any one or more of the metrology functions and may represent any type of communication connection, such as to the internet or any other computer network. Additionally, the metrology functions may be embodied in whole or in part within the circuitry of an application specific integrated circuit (ASIC) or a programmable logic device (PLD), and the functions may be embodied in a computer understandable descriptor language which may be used to create an ASIC or PLD.

The optical metrology device 100 is illustrated by way of example. Other types of optical metrology devices may be used if desired, including spectroscopic or single wavelength devices, ellipsometers, scatterometers, etc.

The optical metrology device 100, as well as all metrology devices, have a system noise level. In order to accurately measure a structure, the strength of the measurement signal must be significantly greater than the system noise level of the metrology device. By way of example, a measurement signal strength that is 10× or greater than the system noise level may be considered sufficiently greater than the system noise level to accurately characterize a structure. If the measurement signal strength is below or comparable to the system noise level of the optical metrology device (i.e., less than 10× the system noise level), isolating the measurement signal from the noise signal may be very difficult or impossible, thereby decreasing the accuracy of the measurement or rendering measurement of the structure impossible.

In many cases, the structure under test may be below one or more light absorbing layers. When the OCD target includes an overlying absorbing layer, the resulting measurement signal from structures below the absorbing layers may be reduced or eliminated so that the measurement signal strength is comparable or below the system noise level of the optical metrology device. In one implementation, the structure under test may belong to the bottom part of the top absorbing layer, in which case the structure under test is not a separate layer that is under the absorbing layer, but is part of the absorbing layer itself. In this instance, because the structure under test is on the bottom of the absorbing layer, the structure under test may still be said to have an absorbing layer disposed over it.

FIGS. 2A and 2B, by way of example, illustrate a perspective view and a cross-sectional side view, respectively, of a conventional OCD target 150 for a 3D semiconductor device. The OCD target 150 includes a regular array of holes 152 in an absorbing layer 154 with a structure 156 to be characterized that is under the absorbing layer 154, where the box 155 with broken lines indicates the layer with the critical structure to be measured. As illustrating in FIG. 2B, the structure 156 may be characterized by height 158. The OCD target 150 is representative of the physical parameters of the 3D semiconductor device under test, such as the pitches for the array of holes 152, thicknesses, widths, sidewall angles. For example, the design of the OCD target 150 should reflect the physical property of the device as closely as possible, but the design of the OCD target 150 may be simplified or changed into regular arrays so that it is possible to measure the OCD target 150, whereas an exact replica of the device under test could not be measured using the optical metrology device. Light from the optical metrology device is incident on the OCD target 150, illustrated by arrows 160. The absorbing layer 154 absorbs the incident light thereby permitting only a reduced amount of light to penetrate to the bottom of the structure 156, as illustrated by small arrows 162. The light that does penetrate to the structure 156 must be returned to the detector of the optical metrology device, and thus, must pass through the absorbing layer 154 a second time. Thus, only a small amount of light is returned to the detector resulting in a measurement signal strength that is less than or comparable to the signal noise level of the optical metrology device. FIG. 2B, by way of example, illustrates the resulting detected light intensity distribution resulting from the structure 156 with curve 164.

FIGS. 3A and 3B, by way of comparison, illustrate a perspective view and a cross-sectional side view, respectively, of an OCD target 200 that is similar to OCD target 200, i.e., OCD target 200 and OCD target 150 are for the same 3D semiconductor device. Physical parameters of OCD target 200, however, have been altered based on parameters of the optical metrology device to be used to measure the OCD target 200 to improve the penetration of incident light and the extraction of the measurement light returned to the optical metrology device. For example, the pitches of the array of holes 202 in the OCD target 200 have been altered based on the photonic band gap to increase the penetration of incident light (illustrated by arrows 210) through the absorbing layer 204 to the structure 206 to be characterized, where the box 205 with broken lines indicates the layer with the critical structure to be measured. As illustrating in FIG. 3B, the structure 206 may be characterized by height 208. As illustrated by large arrows 212, an increased amount of light penetrates the layer 204 to the structure 206 relative to the OCD target 150 shown in FIG. 2A. The light that penetrates to the structure 206 is returned to the detector of the optical metrology device, after passing through the absorbing layer 204 a second time. Due to the changes in the physical parameters of the OCD target 200, a measurement signal is received that is significantly greater (e.g., 10× or greater) than the system noise level of the metrology device. FIG. 3B, by way of example, illustrates the resulting detected light intensity distribution resulting from the structure 206 with curve 209. It should be understood that while some physical parameters of OCD target 200, such as pitches of the array, may be altered with respect to the 3D semiconductor device, the physical parameters of the specific structure of the 3D semiconductor device to be characterized are not altered.

Figure 4:
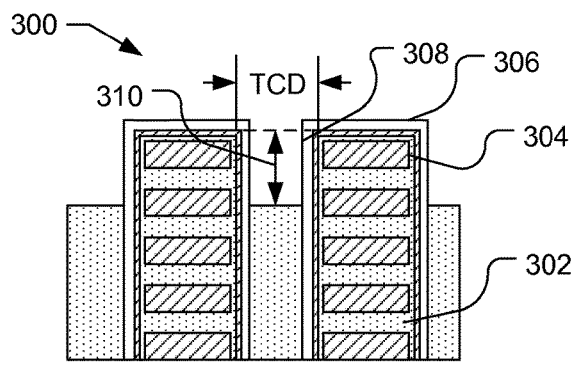
FIG. 4 shows a cross-sectional view of an example of 3D semiconductor device that may be measured using an OCD target as discussed herein.
Figure 5:
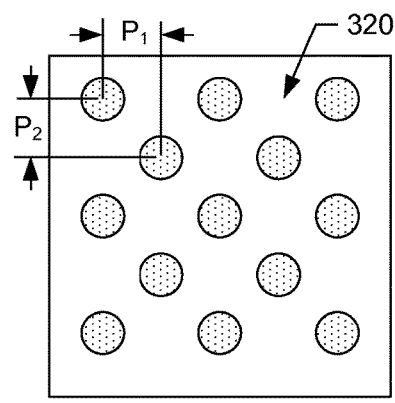
FIG. 5 illustrates a top view of an array of the 3D semiconductor devices from FIG. 4.

FIG. 4 shows a cross-sectional view of an example of 3D semiconductor device 300 that may be measured using an OCD target as discussed herein. The 3D semiconductor device 300 is, e.g., a 3D NAND (VNAND) flash device, that is illustrated as including a plurality of oxide layers 302 and nitride layers 304, covered by an overlying polysilicon layer 306. A hole 308 has a TCD of, e.g., 100 nm, in which there is an oxide recess height 310. FIG. 5 illustrates a top view of an array 320 of the 3D semiconductor devices 300, with a pitch P1 in a first direction and a pitch P2 in a second direction. One important parameter of the 3D semiconductor device 300 to be measured is the oxide recess height 310, which is below the polysilicon layer 306. In a standard OCD target, the physical parameters of the OCD target are based on the parameters of the 3D semiconductor device 300. The absorption of light from the optical metrology device by the polysilicon layer 308 significantly reduces the signal strength from the oxide recess height 310, making the measurement difficult. By altering the physical parameters of the OCD target, such as the pitches $P_1$ and $P_2$ or other physical parameters, the measurement signal strength may be significantly increased to 10× or greater than the system noise level of the metrology device, thereby improving the ability to measure the oxide recess height 310.

It should be understood that the 3D semiconductor device 300 in FIGS. 4 and 5 is illustrated by way of example. OCD targets may be produced as discussed herein for other semiconductor devices, including devices that do not include an overlying absorbing top layer. For example, it may be desirable to produce an OCD target, as discussed herein, for semiconductor structures that have a spectrum response that is comparable to or below the system noise level for the metrology device measurement device due, e.g., to low pattern density or a small volume change. For example, as is well known, in 3D structure, the change of a parameter for some structure, e.g., 1 nm change of the depth of a small hole, results a very small change in total volume when compared to the same amount of change in other parameters, e.g., 1 nm change of the thickness of a continuous film.

Figure 6:
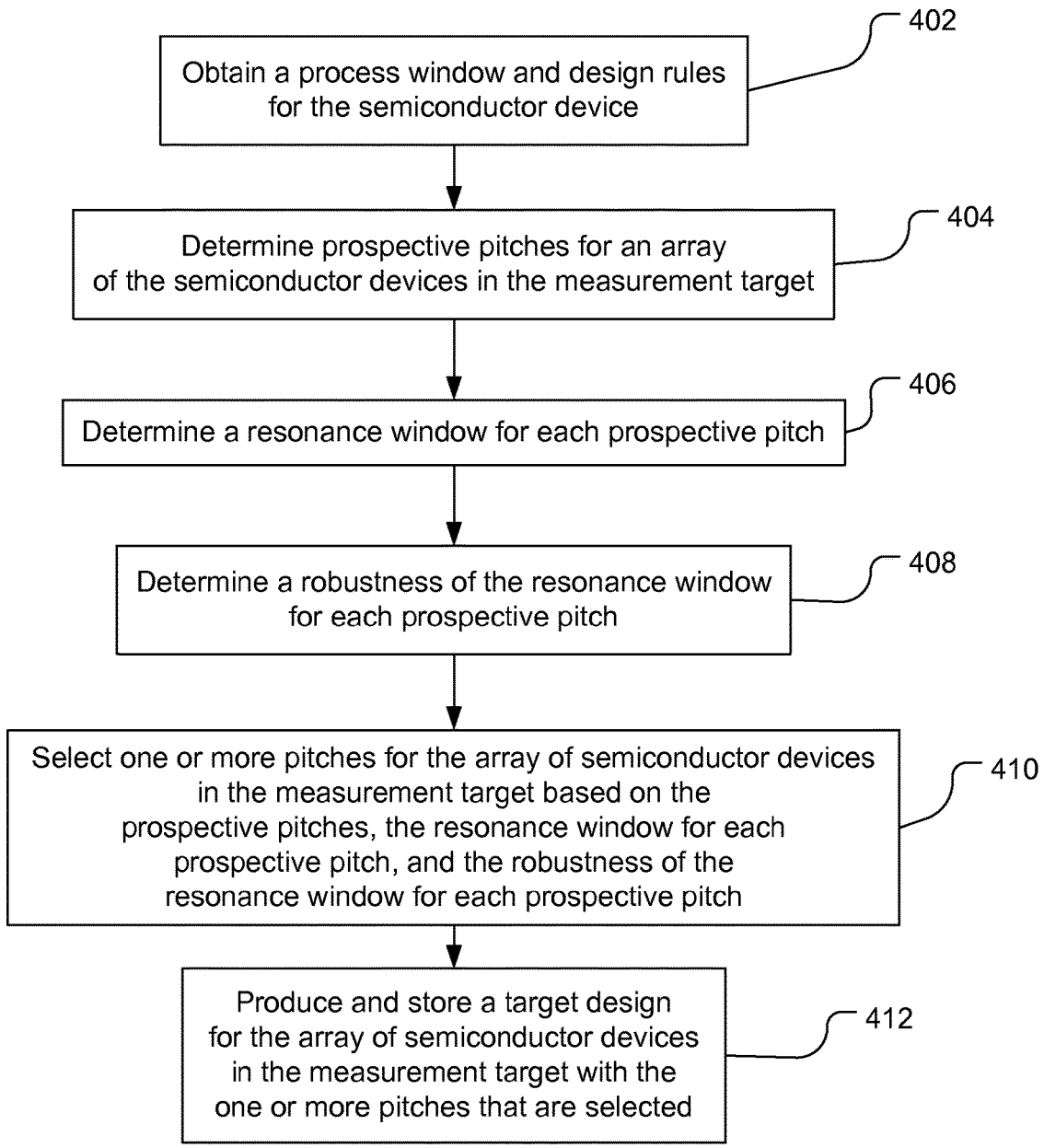
FIG. 6 is a flow chart illustrating a method of designing a measurement target with altered pitches for a semiconductor device to be measured with an optical metrology device.

FIG. 6, by way of example, is a flow chart illustrating a method of designing a measurement target for a semiconductor device to be measured with an optical metrology device. As illustrated, a process window and design rules for the semiconductor device are obtained (402). Process windows and design rules are well known in the art. By way of example of a process window example may be the diameter of the hole, e.g., 80 nm +/−5 nm, and an example of a design rule may be the minimal separation between the holes, e.g., 40 nm. The semiconductor device includes a structure that is to be measured that has a spectrum response that is comparable to or below system noise level for the optical critical dimension measurement device to be used to measure the structure. The spectrum response may be comparable to or below the system noise level for the optical critical dimension measurement device due, e.g., to small volume change, low pattern density, or strong absorption from materials above the structure. By way of example, the semiconductor device may be a three-dimensional NAND flash memory, with an absorbing top layer of polysilicon, and the structure to be measured is an Oxide Recess height.

Prospective pitches for an array of the semiconductor devices in the measurement target are determined (404). The prospective pitches may be determined by modeling the measurement of the structures in the array of semiconductor devices for different pitches of the array to identify pitches that produce a spectrum response from the structures that is at least 10 times greater than a system noise level for the optical critical dimension measurement device. By way of example, the pitches may be identified that produce the spectrum response from the structures that is at least 100 times greater than the system noise level for the optical critical dimension measurement device.

A resonance window for each prospective pitch is determined (406). The resonance window for each prospective pitch may be determined by modeling the measurement of the structures in the array of semiconductor devices for variations of the prospective pitches of the array to identify the variations for the prospective pitches of the array in which the spectrum response from the structures does not decrease by more than a first threshold.

A robustness of the resonance window is determined for each prospective pitch (408). The robustness of the resonance window may be determined by modeling the measurement of the structures in the array of semiconductor devices for variations in design parameters of semiconductor device other than pitch to identify the variations in the design parameters of the array in which the spectrum response from the structures does not decrease by more than a second threshold.

One or more pitches for the array of semiconductor devices in the measurement target are selected based on the prospective pitches, the resonance window for each prospective pitch, and the robustness of the resonance window for each prospective pitch (410). The target design is produced and stored for the array of semiconductor devices in the measurement target with the one or more pitches that are selected (412).

Figure 7:
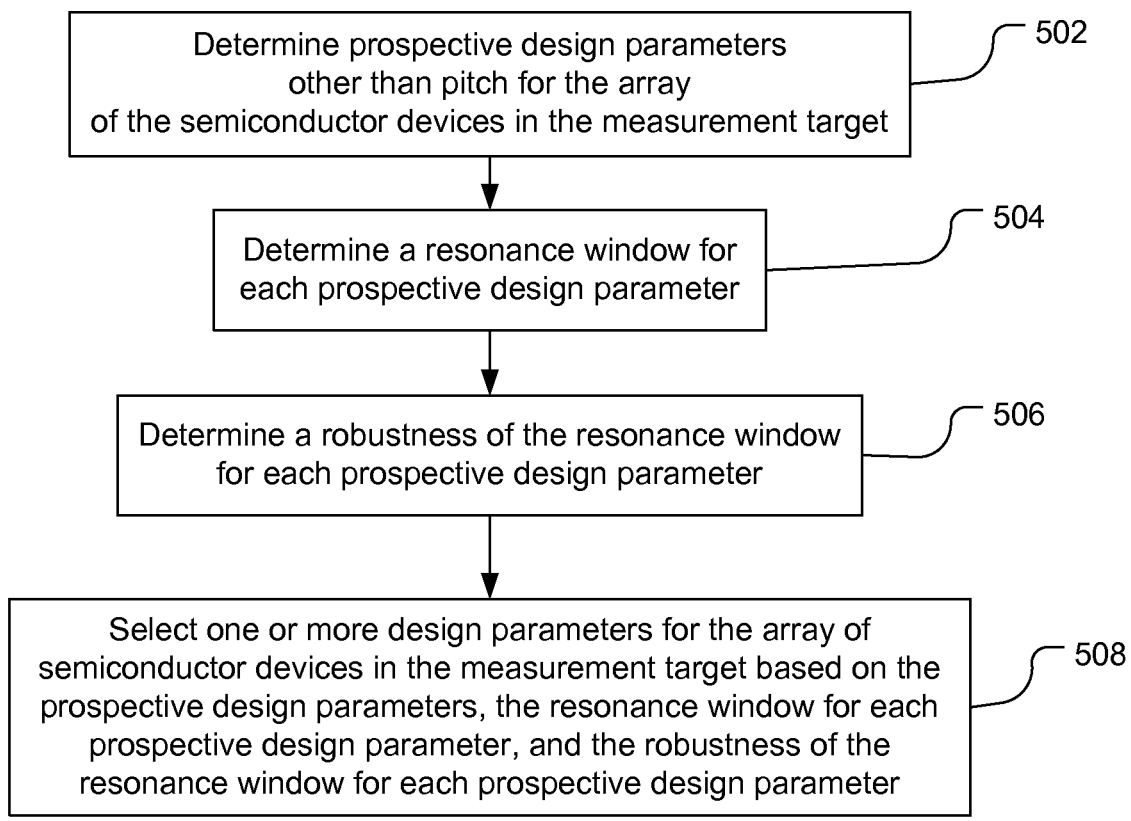
FIG. 7 is a flow chart illustrating a method of designing a measurement target with altered design parameters for a semiconductor device to be measured with an optical metrology device that may be used in addition to the method shown in FIG. 6.

FIG. 7 is a flow chart illustrating a method of designing a measurement target for a semiconductor device to be measured with an optical metrology device that may be used in addition to the method shown in FIG. 6. As illustrated, prospective design parameters other than pitch for the array of semiconductor devices are determined (502). The prospective design parameters other than pitch may be determined by modeling the measurement of the structures in the array of semiconductor devices for different design parameters of the array to identity design parameters that when combined with the prospective pitches produce the spectrum response from the structures that is at least 10 times greater than the system noise level for the optical critical dimension measurement device. By way of example, the prospective design parameters include critical dimensions and thickness of structures other than the structure to be characterized by the optical metrology device.

A resonance window for each prospective design parameter is determined (504). The resonance window for each prospective design parameter may be determined by modeling the measurement of the structures in the array of semiconductor devices for variations of the prospective design parameters of the array to identify the variations for the prospective design parameters in which the spectrum response from the structures does not decrease by more than a third threshold.

A robustness of the resonance window for each prospective design parameter is determined (506). The robustness of the resonance window for each prospective design parameter may be determined by modeling the measurement of the structures in the array of semiconductor devices for variations in other design parameters of the array to identify the variations in the other design parameters of the array in which the spectrum response from the structures does not decrease by more than a fourth threshold.

One or more design parameters for the array of semiconductor devices is selected based on the prospective design parameters, the resonance window for each prospective design parameter, and the robustness of the resonance window for each prospective design parameter (508). The target design produced and stored in block 412 in FIG. 6 further uses the selected one or more design parameters.

Figure 8:
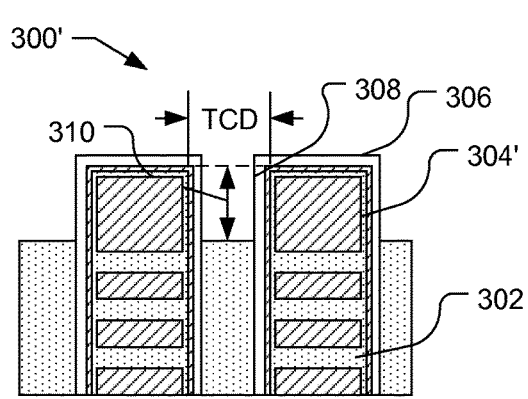
FIG. 8 illustrates a cross sectional view of a semiconductor device in a measurement target.
Figure 9:
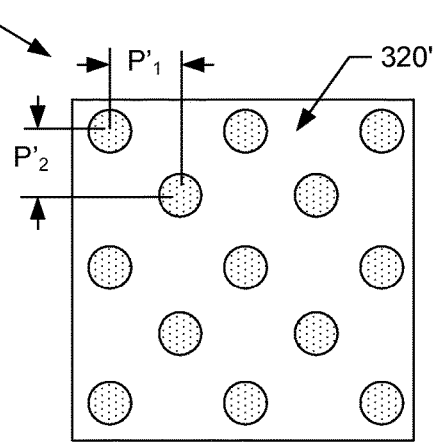
FIG. 9 illustrate a top view of an array of the semiconductor devices from FIG. 8 produced in a measurement target in accordance with the methods discussed in FIG. 6 and optionally in accordance with the method discussed in FIG. 7.

FIGS. 8 and 9 illustrate a cross sectional view of a single semiconductor device 300' and a top view of an array 320' of the semiconductor devices produced in a measurement target 600 in accordance with the method discussed in FIG. 6 and optionally in accordance with the method discussed in FIG. 7. The semiconductor device 300' and the array 320' shown in FIGS. 8 and 9 are similar to the semiconductor device 300 and array 320 shown in FIGS. 4 and 5, like designated elements being the same. The measurement target 600 is for the semiconductor device 300 shown in FIG. 4 having a structure, e.g., oxide recess height 310, to be characterized by measurement. As illustrated in the figures, the structure 310 is below a layer 306 that is at least partially absorbing of wavelengths of light used by an optical critical dimension measurement device. As illustrated, the array of semiconductor devices may be three-dimensional NAND flash memory, but the array may be for other semiconductor devices.

As illustrated in FIG. 9, the measurement target 600 includes a two-dimensional array 320' of the semiconductor devices 300' comprising an array of holes in the layer having a first pitch $P'_1$ in a first direction and a second pitch $P'_2$ in a second direction that is different than the first direction. Each semiconductor device in the two-dimensional array of semiconductor devices includes the structure 310 aligned with a hole 308 in the layer 306, wherein a parameter of the structure is measured during the optical critical dimension measurement of the array of semiconductor device. The first pitch $P'_1$ and the second pitch $P'_2$ of the two-dimensional array 320' of holes in the layer are configured to produce a spectrum response from the structures that is at least 10 times greater than a system noise level for the optical critical dimension measurement device and that is at least 10 times greater than a spectrum response produced by structures having a same parameter and that is underlying a two-dimensional array of holes 320 having any other pitch in the first direction and any other pitch in the second direction. By way of example, the first pitch $P'_1$ and the second pitch $P'_2$ may be the same. The first pitch $P'_1$ and the second pitch $P'_2$ of the two-dimensional array 320' of holes in the layer may be designed by the process discussed in FIG. 6, wherein after producing and storing the target design, the measurement target is manufactured based on the target design. Additionally, if desired, design parameters other than pitch for the array of semiconductor devices, e.g., layer 304' in FIG. 8, may be designed by the process discussed in FIG. 7.

Figure 10:
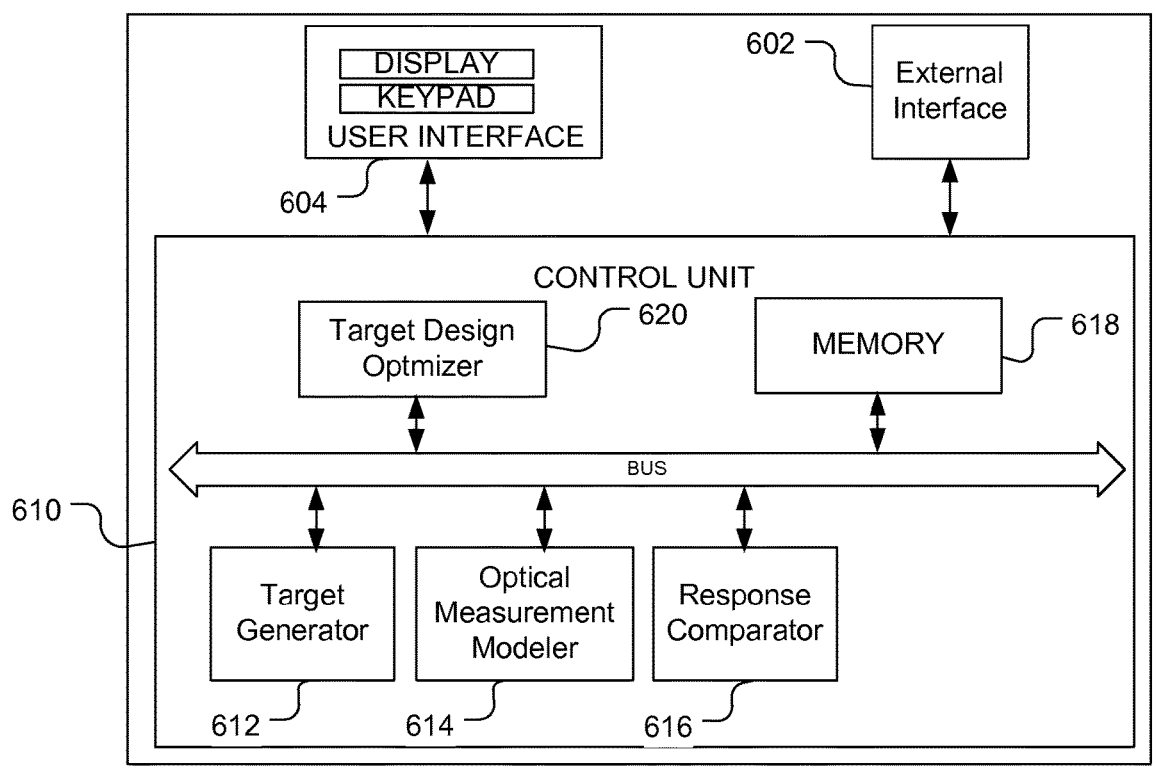
FIG. 10 is a block diagram of the processor capable of designing a measurement target for a semiconductor device to be measured with an optical metrology device in accordance with the method discussed in FIG. 6 and optionally in accordance with the method discussed in FIG. 7.

FIG. 10 is a block diagram of the processor 600 capable of designing a measurement target for a semiconductor device to be measured with an optical metrology device in accordance with the method discussed in FIG. 6 and optionally in accordance with the method discussed in FIG. 7. The processor 600, by way of example, may be coupled to an optical metrology device or may be a stand-alone device. The processor 600 includes an external interface 602 capable of receiving process window and design rules for the semiconductor device. The external interface 602 may be, e.g., a DVD drive, USB port, IEEE 1394 interface, network, etc. The external interface 602 may also be capable of providing the resulting target design. The processor 600 may further include a user interface 604 that may include e.g., a display, as well as a keypad or other input device through which the user can input information into the processor 600.

The processor also includes a control unit 610 that is connected to and communicates with the external interface 602 and user interface 604. The control unit 610 obtains the process window and design rules for the semiconductor device and generates the resulting target design. The control unit 610, for example, may include a target generator 612, which produces targets with arrays of the semiconductor devices having different pitches and variations in design parameters of semiconductor device based on the process window and design rules for the semiconductor device. The control unit 610 further includes an optical measurement modeler 614 that models the spectrum response from targets produced by the target generator 612 as discussed in FIG. 6. A response comparator 616 is included in the control unit 610 to compare the spectrum response from the optical measurement modeler 614 to the system noise level for the optical metrology device, which may be provided via external interface 602 and stored in memory 618 in order to identify prospective pitches, which may be stored in memory 618. The response comparator 616 may additionally compare changes in spectrum responses for variations in the prospective pitches to a threshold stored in memory 618 to identify the resonance window for each prospective pitch, which may also be stored in memory 618. The response comparator 616 may additionally compare changes in the spectrum response for variations in the design parameters of the semiconductor device to a threshold stored in memory 618 to identify the robustness of the resonance window for each prospective pitch, which may also be stored in memory 618. A target design optimizer 620 selects the one or more pitches for the array of semiconductor devices in the measurement target based on the prospective pitches, the resonance window for each prospective pitch, and the robustness of the resonance window for each prospective pitch and the resulting target design is stored in memory 618.

It will be understood as used herein that the processor 600 can, but need not necessarily include, one or more microprocessors, embedded processors, controllers, application specific integrated circuits (ASICs), digital signal processors (DSPs), and the like. The description of the processor 600 is intended to describe the functions that are implemented rather than specific hardware. Moreover, as used herein the term "memory" refers to any type of computer storage medium, including long term, short term, or other memory associated with the mobile device, and is not to be limited to any particular type of memory or number of memories, or type of media upon which memory is stored.

The methodologies described herein may be implemented by various means depending upon the application. For example, these methodologies may be implemented in hardware, firmware, software, or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in memory 618 and executed by the processor. Memory 618 may be implemented within or external to the processor 618. If implemented in firmware and/or software, the functions may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

The data structures and software code for implementing one or more acts described in this detailed description can be implemented by one of ordinary skill in the art in light of the present disclosure and stored, e.g., on a computer readable storage medium, such as memory 618, which may be any non-transitory device or medium that can store code and/or data for use by a computer system such as processor 600. The computer-usable storage medium 618 may be, but is not limited to, magnetic and optical storage devices such as disk drives, magnetic tape, compact discs, and DVDs (digital versatile discs or digital video discs). A communication port may also be used to receive instructions that are stored in memory or other storage in processor 600 and used to program the computer 600 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 11:
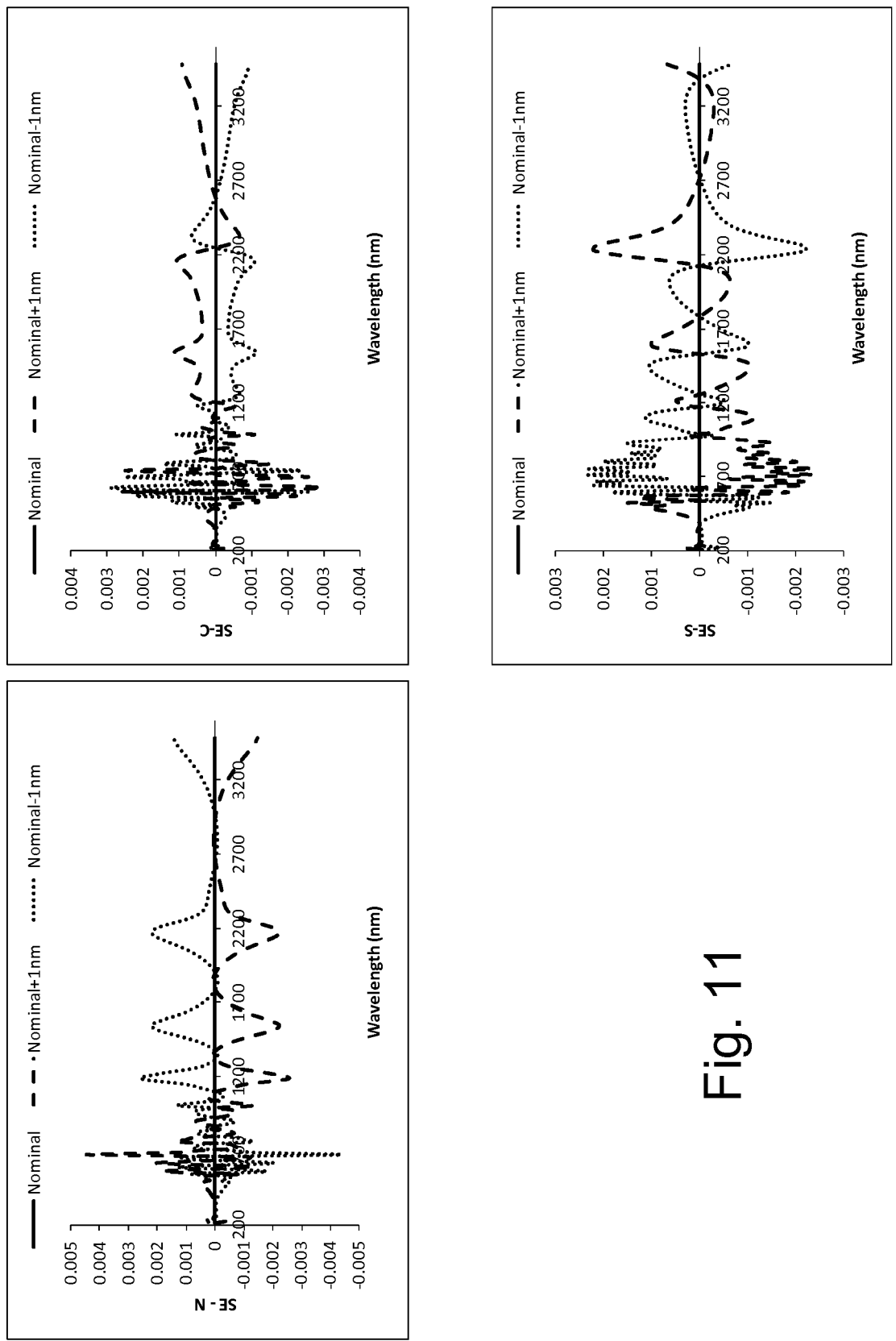
FIG. 11 illustrates a simulated signal strength for a standard OCD target.
Figure 12:
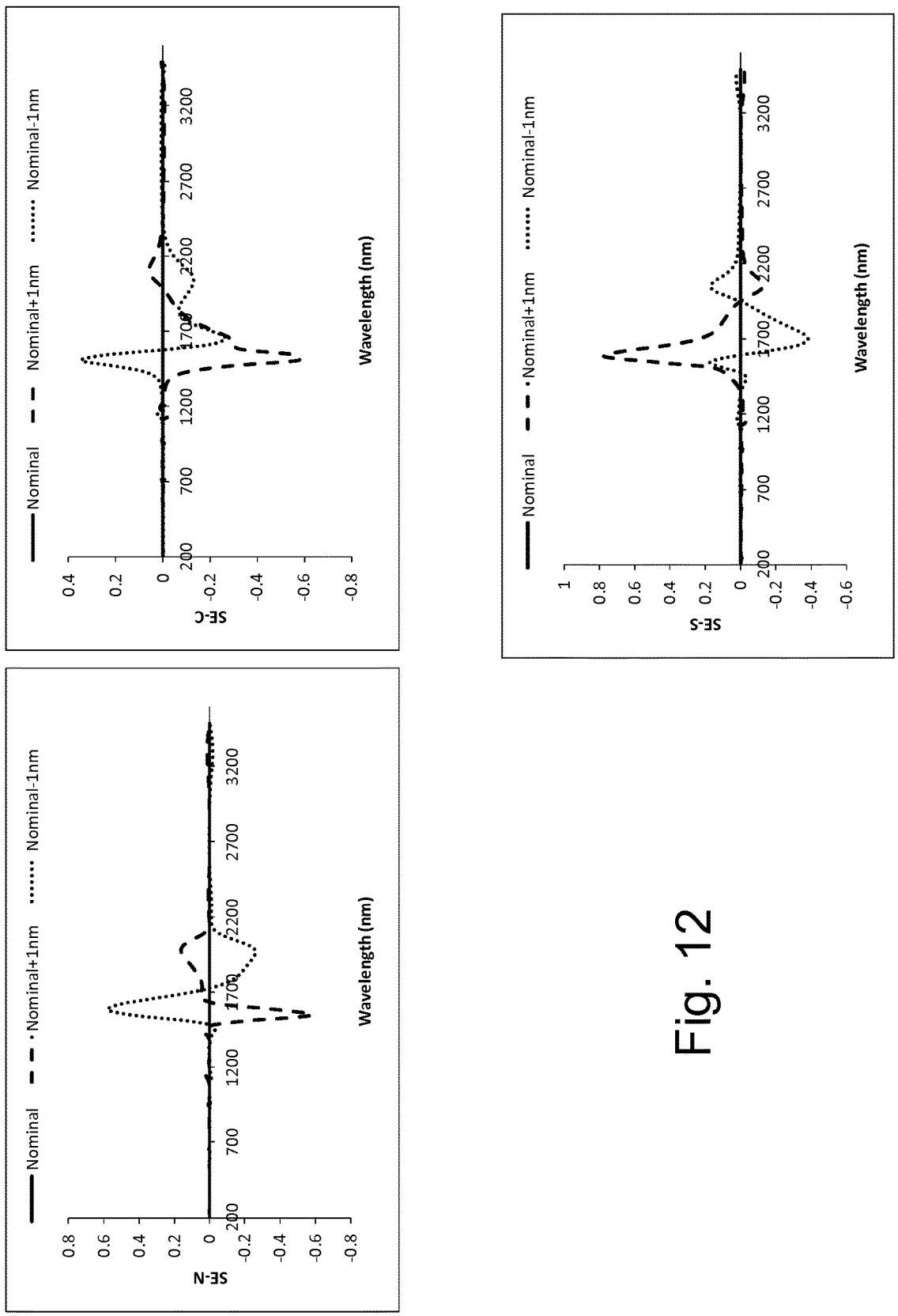
FIG. 12 illustrates the simulated signal strength for an OCD target that has been altered as discussed herein.

FIG. 11 illustrates a simulated signal strength for a standard OCD target and FIG. 12 illustrates the simulated signal strength for an OCD target that has been altered as discussed herein. The charts of FIGS. 11 and 12 include graphs for nominal, nominal+1 nm and nominal−1 nm oxide recess height in the array. As can be seen, the spectroscopic ellipsometer signal from the standard target is on the order of 0.002, which is the same level of system noise. As illustrated in FIG. 12, with an OCD target that has been altered as discussed herein, the signal strength has 100× improvement at a broad wavelength range, which enables the OCD measurement of the OCD structure.

Figure 13A:
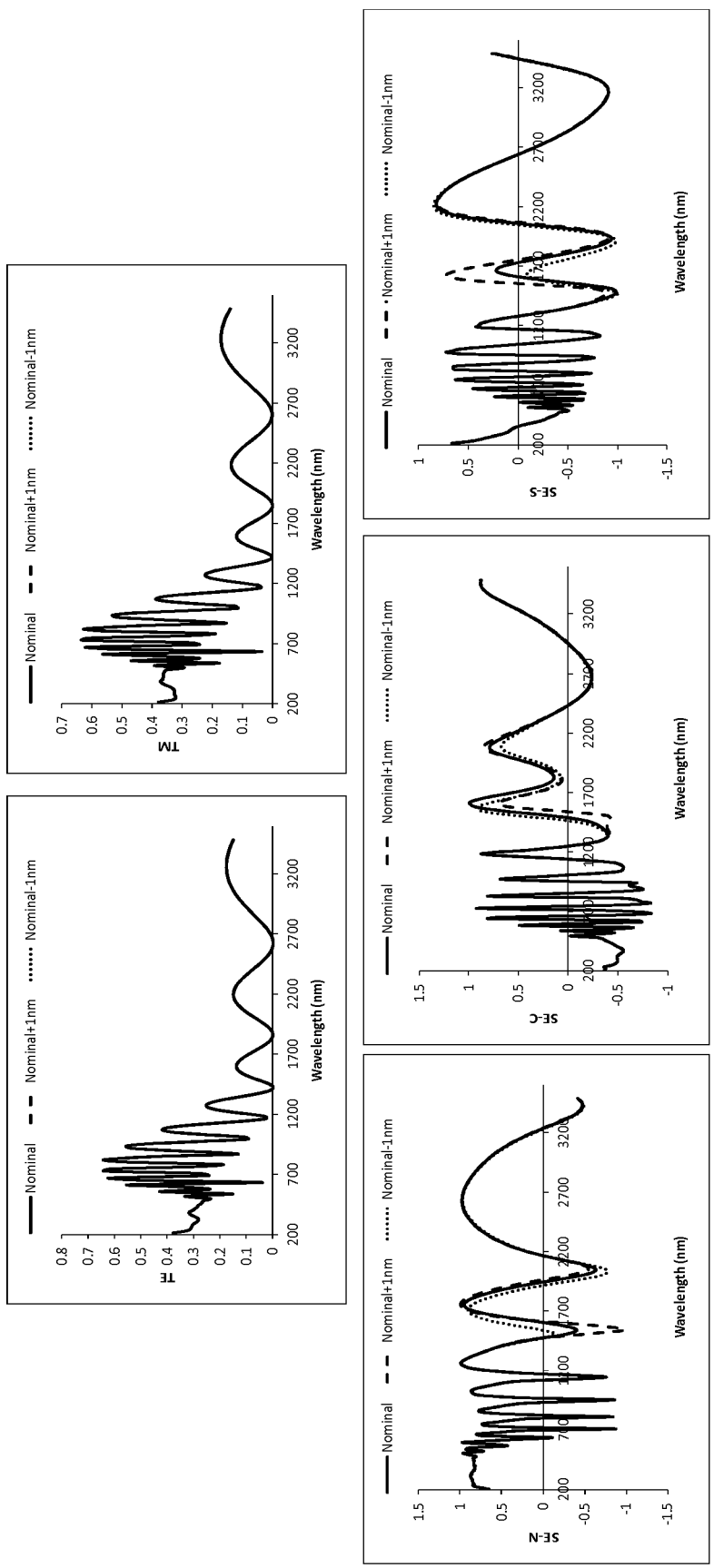
FIGS. 13A and 13B illustrate simulated spectroscopic ellipsometer (SE) spectra and SE sensitivity to oxide recess for an OCD target with pitches that have been altered as discussed herein.
Figure 13B:
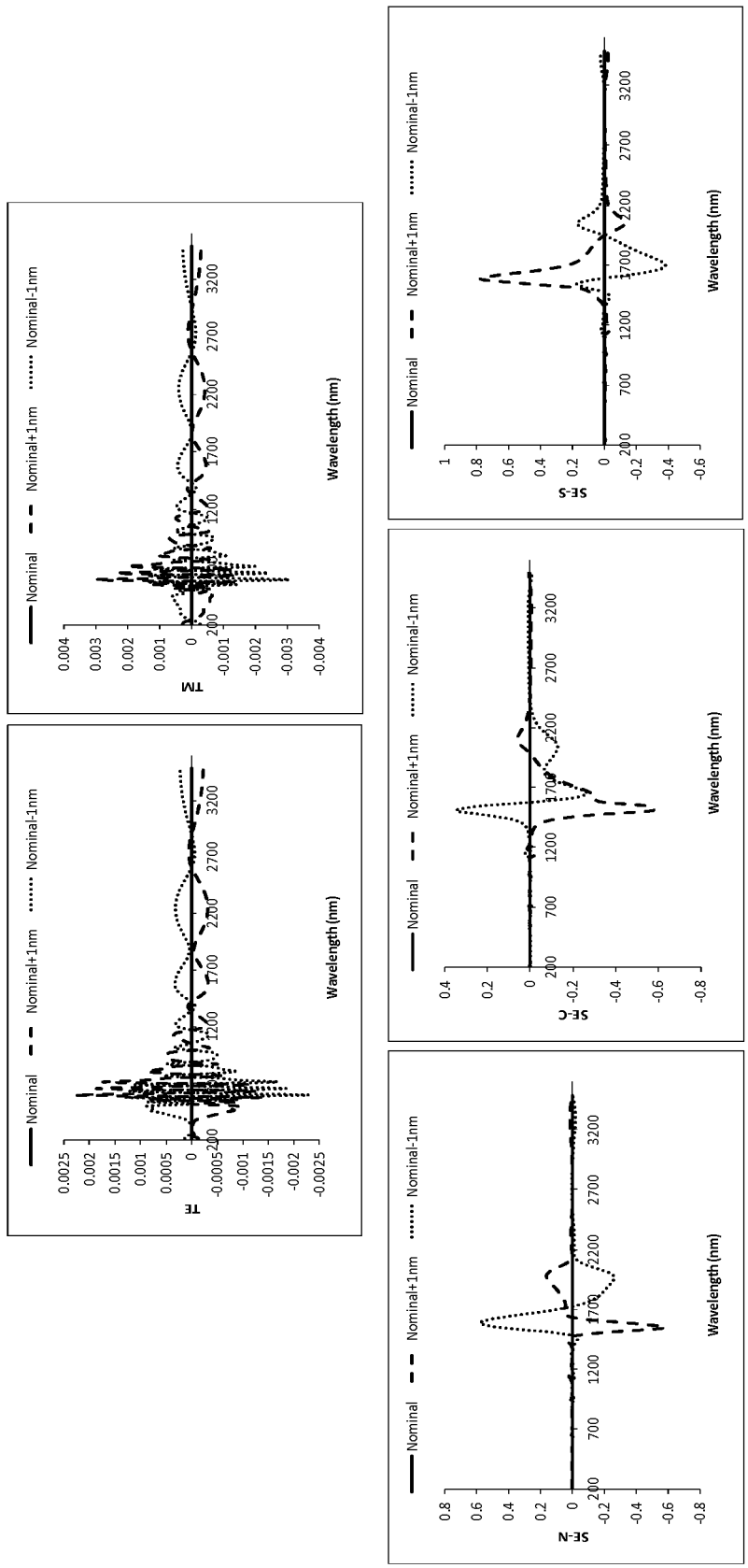
Figure 14A:
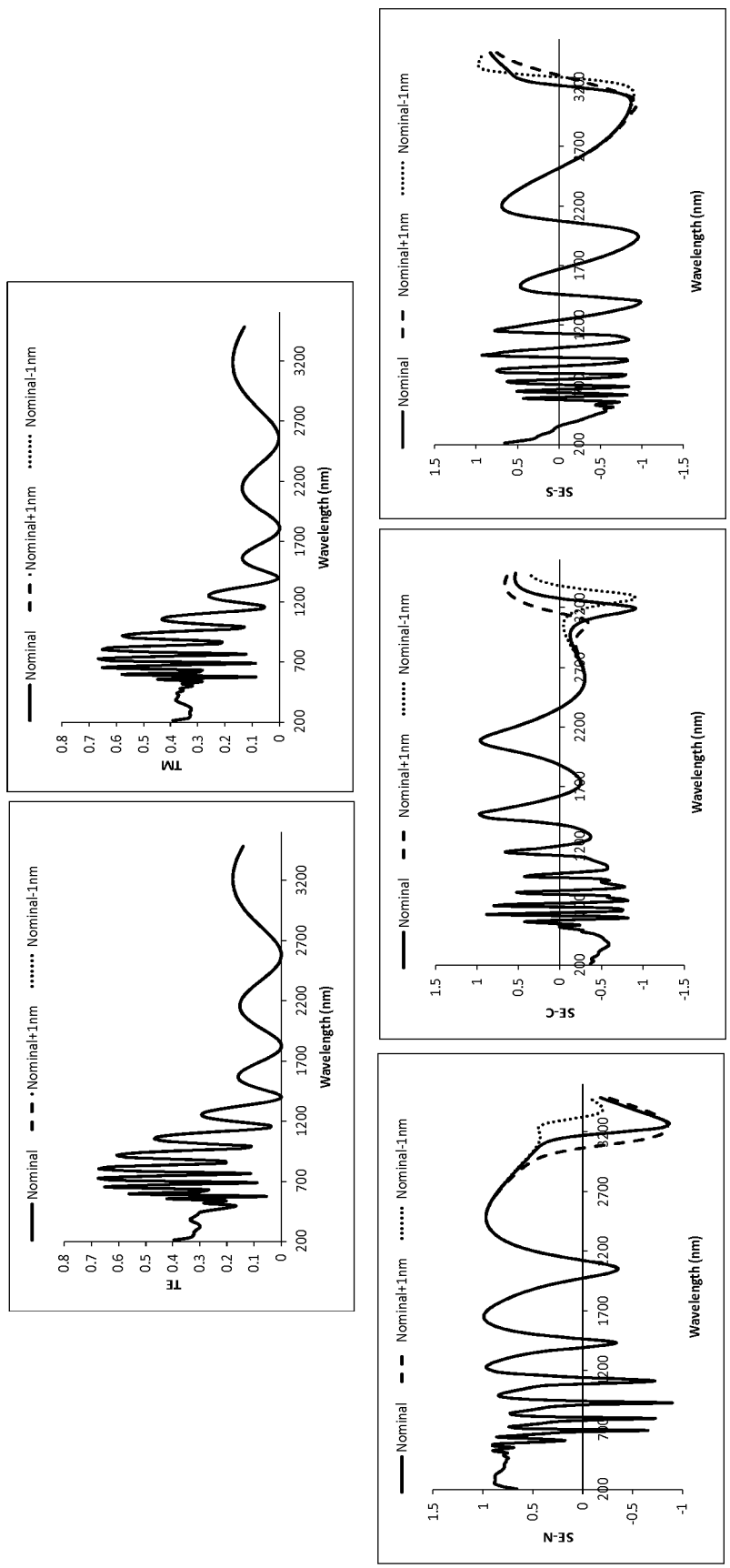
FIGS. 14A and 14B illustrate simulated SE spectra and SE sensitivity to oxide recess for an OCD target with another set of pitches that have been altered as discussed herein.
Figure 14B:
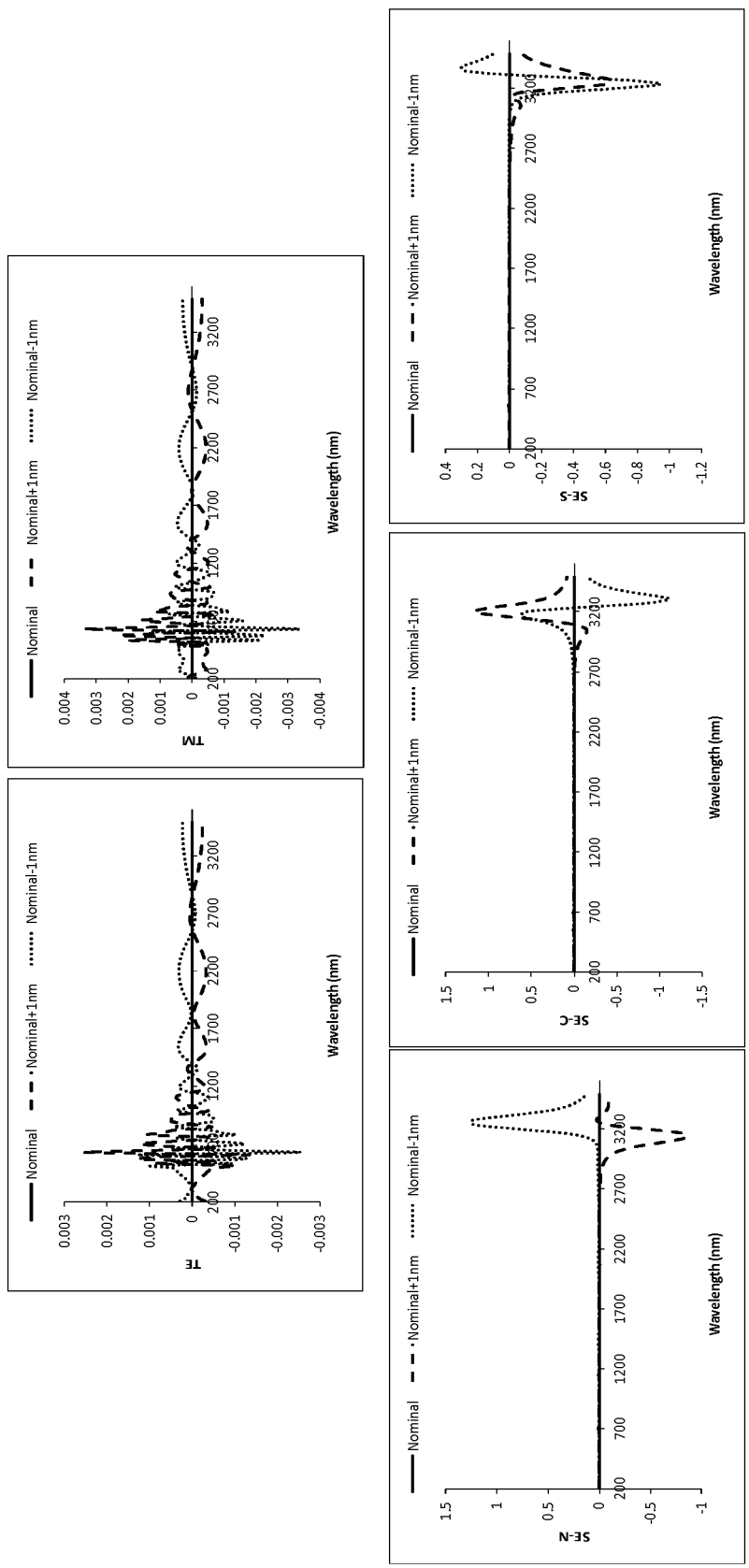
Figure 15A:
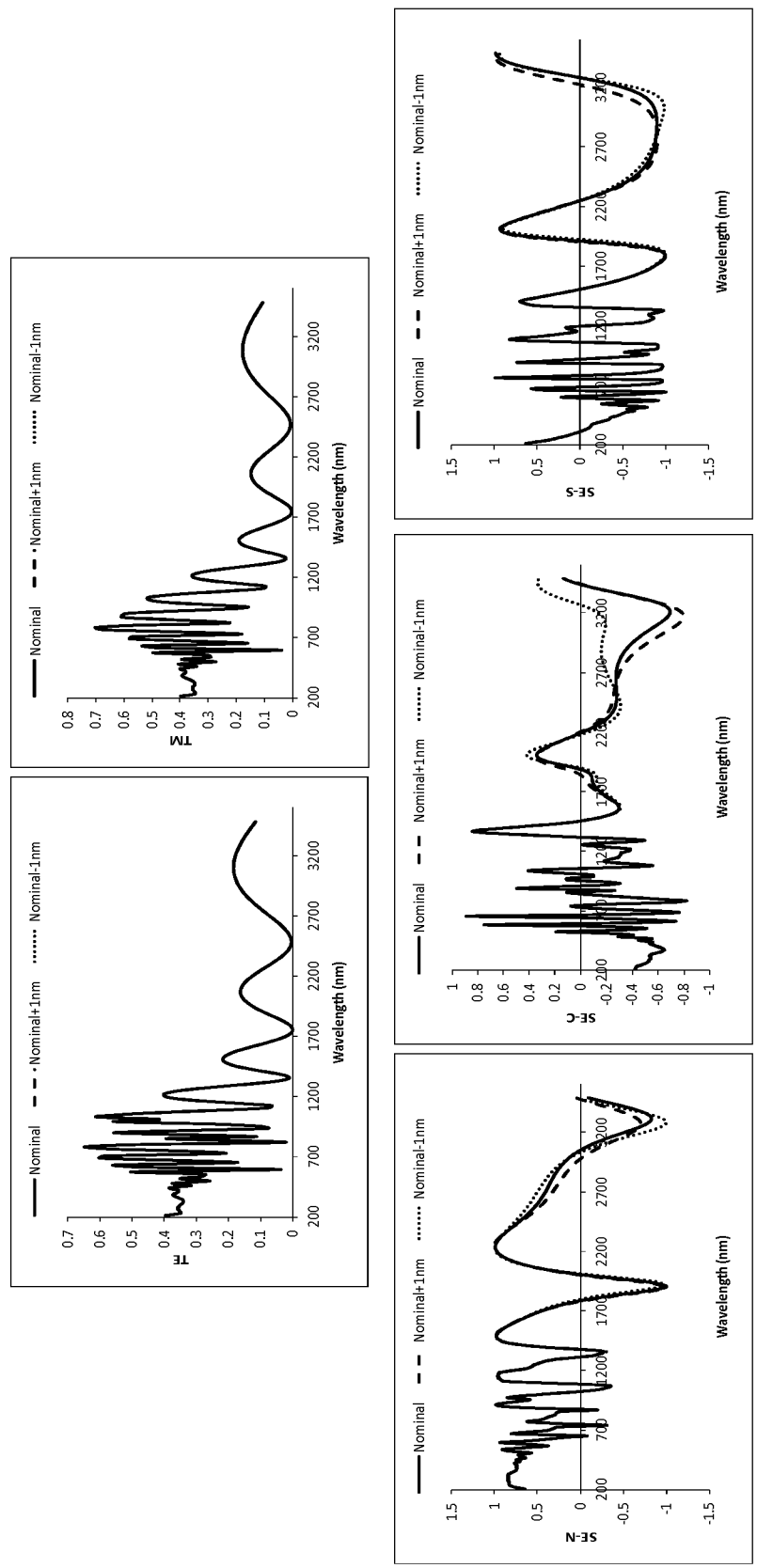
FIGS. 15A and 15B illustrate simulated SE spectra and SE sensitivity to oxide recess for an OCD target with another set of pitches that have been altered as discussed herein.
Figure 15B:
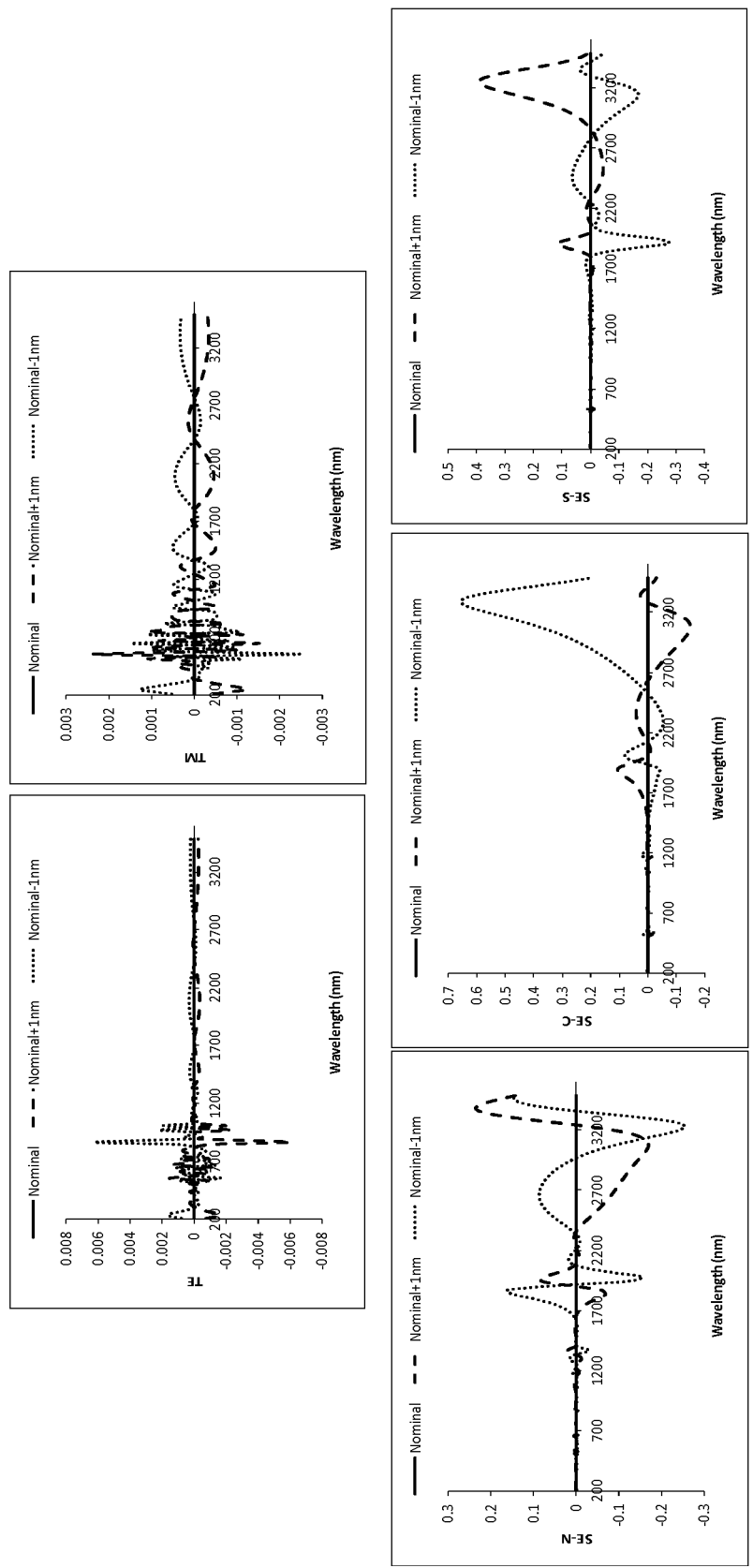

Similarly, FIGS. 13A, 14A, and 15A illustrate simulated spectroscopic ellipsometer (SE) spectra for an OCD targets that have been altered as discussed herein, with pitches of 245×245 nm, 290×290 nm, and 715×715 nm, respectively, including graphs for nominal, nominal+1 nm and nominal−1 nm oxide recess height in the array. FIGS. 13B, 14B, and 15B illustrate the simulated signal strength for the same OCD targets by subtracting the spectrum of nominal oxide recess height from the spectra of nominal, nominal+1 nm and nominal−1 nm oxide recess height. Thus, it can been that there are multiple pitches that may provide an enhanced spectrum response.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of designing a measurement target for a semiconductor device, the method comprising:
obtaining a process window and design rules for the semiconductor device, wherein the semiconductor device comprises a structure to be measured that has a spectrum response that is comparable to or below system noise level for an optical critical dimension measurement device to be used to measure the structure;
determining prospective pitches for an array of the semiconductor devices in the measurement target based on the process window and design rules by modeling the measurement of the structures in the array of semiconductor devices for different pitches of the array to identify pitches that produce a spectrum response from the structures that is at least 10 times greater than a system noise level for the optical critical dimension measurement device;
determining a resonance window for each prospective pitch by modeling the measurement of the structures in the array of semiconductor devices for variations of the prospective pitches of the array to identify the variations for the prospective pitches of the array in which the spectrum response from the structures does not decrease by more than a first threshold;
determining a robustness of the resonance window for each prospective pitch by modeling the measurement of the structures in the array of semiconductor devices for variations in design parameters of semiconductor device other than pitch to identify the variations in the design parameters of the array in which the spectrum response from the structures does not decrease by more than a second threshold;
selecting one or more pitches for the array of semiconductor devices in the measurement target based on the prospective pitches, the resonance window for each prospective pitch, and the robustness of the resonance window for each prospective pitch; and
producing and storing a target design for the array of semiconductor devices in the measurement target with the one or more pitches that are selected.

2. The method of claim 1, wherein determining the prospective pitches for the array of the semiconductor device comprises identifying pitches that produce the spectrum response from the structures that is at least 100 times greater than the system noise level for the optical critical dimension measurement device.

3. The method of claim 1, wherein the structure in the semiconductor device has the spectrum response that is comparable to or below the system noise level for the optical critical dimension measurement device due to small volume change, low pattern density, or strong absorption from materials above the structure.

4. The method of claim 1, further comprising:
determining prospective design parameters other than pitch for the array of semiconductor devices by modeling the measurement of the structures in the array of semiconductor devices for different design parameters of the array to identity design parameters that when combined with the prospective pitches produce the spectrum response from the structures that is at least 10 times greater than the system noise level for the optical critical dimension measurement device;
determining a resonance window for each prospective design parameter by modeling the measurement of the structures in the array of semiconductor devices for variations of the prospective design parameters of the array to identify the variations for the prospective design parameters in which the spectrum response from the structures does not decrease by more than a third threshold;
determining a robustness of the resonance window for each prospective design parameter by modeling the measurement of the structures in the array of semiconductor devices for variations in other design parameters of the array to identify the variations in the other design parameters of the array in which the spectrum response from the structures does not decrease by more than a fourth threshold;
selecting one or more design parameters for the array of semiconductor devices based on the prospective design parameters, the resonance window for each prospective design parameter, and the robustness of the resonance window for each prospective design parameter; and
wherein producing and storing the target design for the array of semiconductor devices further uses the selected one or more design parameters.

5. The method of claim 4, wherein the prospective design parameters comprises critical dimensions and thickness.

6. The method of claim 1, wherein the semiconductor device comprises a three-dimensional NAND flash memory with an absorbing top layer of polysilicon, and the structure to be measured is an Oxide Recess height.

7. A measurement target for a semiconductor device having a structure to be characterized by measurement, the structure is below a layer that is at least partially absorbing of wavelengths of light used by an optical critical dimension measurement device, the measurement target comprising:
a two-dimensional array of the semiconductor devices comprising an array of holes in the layer having a first pitch in a first direction and a second pitch in a second direction that is different than the first direction;
each semiconductor device in the two-dimensional array of semiconductor devices comprises the structure aligned with a hole in the layer, wherein a parameter of the structure is measured during the optical critical dimension measurement of the array of semiconductor;
wherein the first pitch and the second pitch of the two-dimensional array of holes in the layer are configured so that variations from nominal for the first pitch and the second pitch does not decrease a spectrum response from the structures by more than a threshold, and to produce a spectrum response from the structures that is at least 10 times greater than a system noise level for the optical critical dimension measurement device and that is at least 10 times greater than a spectrum response produced by structures having a same parameter and that is underlying a two-dimensional array of holes having any other pitch in the first direction and any other pitch in the second direction.

8. The measurement target of claim 7, wherein the first pitch and the second pitch are the same.

9. The measurement target of claim 7, wherein the first pitch and the second pitch of the two-dimensional array of holes in the layer are designed by:
obtaining a process window and design rules for semiconductor device;
determining prospective pitches for the array of semiconductor devices based on the process window and design rules by modeling the measurement of the structures in the array of semiconductor devices for different pitches of the array to identify pitches that produce the spectrum response from the structures that is at least 10 times greater than the system noise level for the optical critical dimension measurement device;
determining a resonance window for each prospective pitch by modeling the measurement of the structures in the array of semiconductor devices for variations of the prospective pitches of the array to identify the variations for the prospective pitches of the array in which the spectrum response from the structures does not decrease by more than a first threshold;
determining a robustness of the resonance window for each prospective pitch by modeling the measurement of the structures in the array of semiconductor devices for variations in design parameters of the array of semiconductor devices other than pitch of the array to identify the variations in the design parameters of the array in which the spectrum response from the structures does not decrease by more than a second threshold;
selecting one or more pitches for the array of semiconductor devices in the measurement target based on the prospective pitches, the resonance window for each prospective pitch, and the robustness of the resonance window for each prospective pitch;
producing and storing a target design for the array of semiconductor devices in the measurement target with the one or more pitches that are selected; and
manufacturing the measurement target based on the target design.

10. The measurement target of claim 9, wherein each semiconductor device in the array of semiconductor devices is designed by:
determining prospective design parameters other than pitch for the array of semiconductor devices by modeling the measurement of the structures in the array of semiconductor devices for different design parameters of the array to identity design parameters that when combined with the prospective pitches produce the spectrum response from the structures that is at least 10 times greater than the system noise level for the optical critical dimension measurement device;
determining a resonance window for each prospective design parameter by modeling the measurement of the structures in the array of semiconductor devices for variations of the prospective design parameters of the array to identify the variations for the prospective design parameters in which the spectrum response from the structures does not decrease by more than a third threshold;

determining a robustness of the resonance window for each prospective design parameter by modeling the measurement of the structures in the array of semiconductor devices for variations in other design parameters of the array to identify the variations in the other design parameters of the array in which the spectrum response from the structures does not decrease by more than a fourth threshold;

selecting one or more design parameters for the array of semiconductor devices based on the prospective design parameters, the resonance window for each prospective design parameter, and the robustness of the resonance window for each prospective design parameter; and wherein producing and storing the target design for the array of semiconductor devices in the measurement target further uses the selected one or more design parameters.

11. The measurement target of claim 7, wherein the array of semiconductor devices comprises three-dimensional NAND flash memory, the layer is polysilicon, and the parameter of the underlying structure to be measured is an Oxide Recess height.

* * * * *